(12) United States Patent
Sato et al.

(10) Patent No.: US 10,150,244 B2
(45) Date of Patent: Dec. 11, 2018

(54) DENTAL APPLIANCES WITH SHAPED MATERIAL COMPONENTS

(71) Applicant: Align Technology, Inc., San Jose, CA (US)

(72) Inventors: Jun Sato, Sunnyvale, CA (US); Ryan Kimura, San Jose, CA (US); Yaser Shanjani, San Jose, CA (US)

(73) Assignee: Align Technology, Inc., San Jose, CA (US)

(*) Notice: Subject to any disclaimer, the term of this patent is extended or adjusted under 35 U.S.C. 154(b) by 65 days.

(21) Appl. No.: 15/298,830

(22) Filed: Oct. 20, 2016

(65) Prior Publication Data

US 2018/0110591 A1    Apr. 26, 2018

(51) Int. Cl.

| | |
|---|---|
| *B29C 53/04* | (2006.01) |
| *A61C 7/08* | (2006.01) |
| *A61C 7/00* | (2006.01) |
| *B29C 53/02* | (2006.01) |
| *B29C 53/36* | (2006.01) |
| *B29C 53/06* | (2006.01) |
| *B29L 31/00* | (2006.01) |
| *B65H 45/00* | (2006.01) |
| *A61C 7/10* | (2006.01) |
| *A61C 13/00* | (2006.01) |

(52) U.S. Cl.
CPC .............. *B29C 53/04* (2013.01); *A61C 7/002* (2013.01); *A61C 7/08* (2013.01); *B29C 53/02* (2013.01); *B29C 53/043* (2013.01); *B29C 53/06* (2013.01); *B29C 53/36* (2013.01); *A61C 7/10* (2013.01); *A61C 13/0013* (2013.01); *B29L 2031/753* (2013.01); *B65H 45/00* (2013.01)

(58) Field of Classification Search
CPC ... A61C 7/08; A61C 7/10; B29C 53/02–53/12
See application file for complete search history.

(56) References Cited

U.S. PATENT DOCUMENTS

| | | | |
|---|---|---|---|
| 2003/0054316 A1* | 3/2003 | Cozzi | A61C 9/0006 433/37 |
| 2016/0230007 A1* | 8/2016 | Johnson | C08L 23/16 |
| 2017/0065373 A1* | 3/2017 | Martz | B33Y 80/00 |
| 2018/0153648 A1* | 6/2018 | Shanjani | A61C 7/10 |

* cited by examiner

*Primary Examiner* — Benjamin A Schiffman
(74) *Attorney, Agent, or Firm* — Brooks, Cameron & Huebsch, PLLC

(57) ABSTRACT

The present disclosure provides method, computing device readable medium, and devices for dental appliances formed with folded material components. An example of a method of forming a dental appliance, includes forming a shell having a number of tooth apertures configured to receive and reposition a number of teeth of a patient along one jaw of a patient, the shell having a number of specialized components and wherein the number of specialized components are formed from folding multiple sections of the first sheet of material over each other.

16 Claims, 9 Drawing Sheets

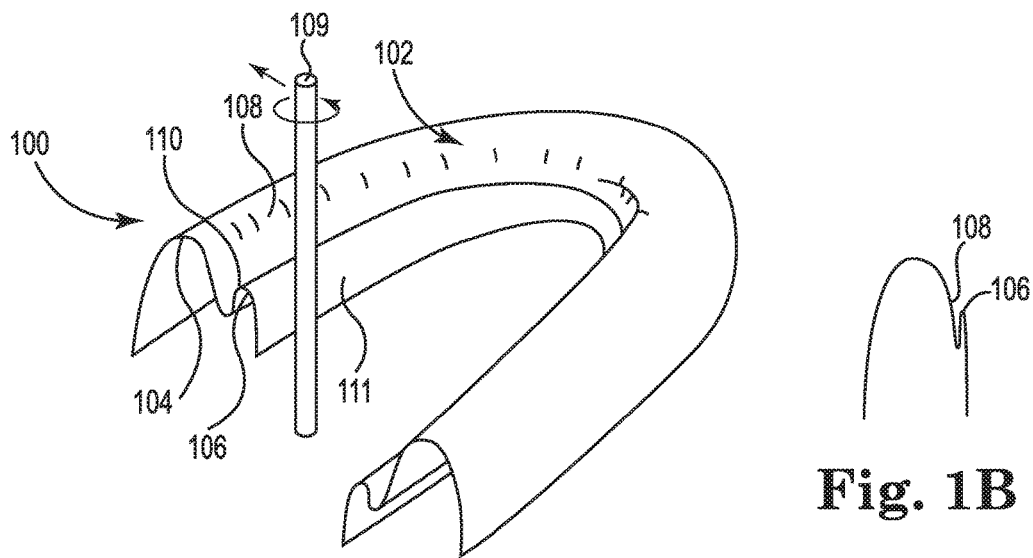
Fig. 1A
Fig. 1B
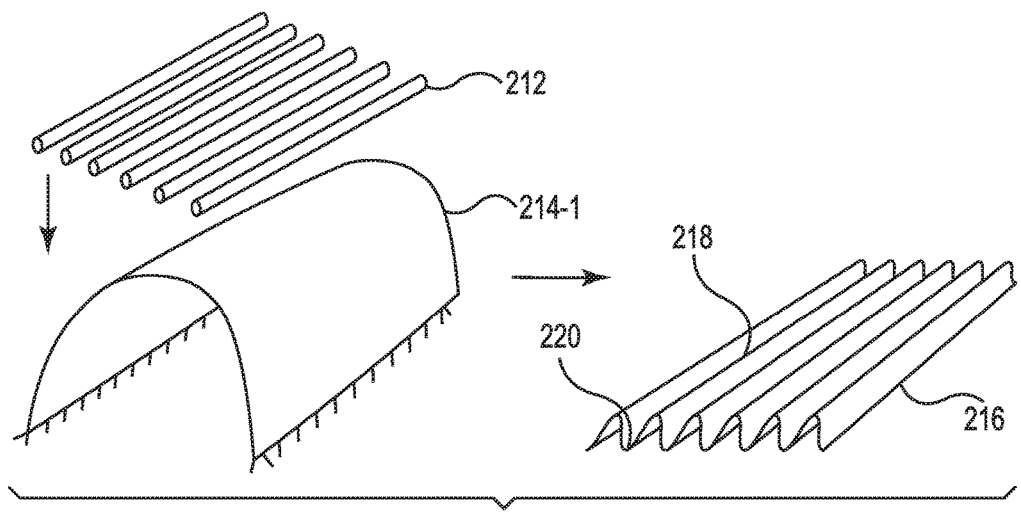
Fig. 2A
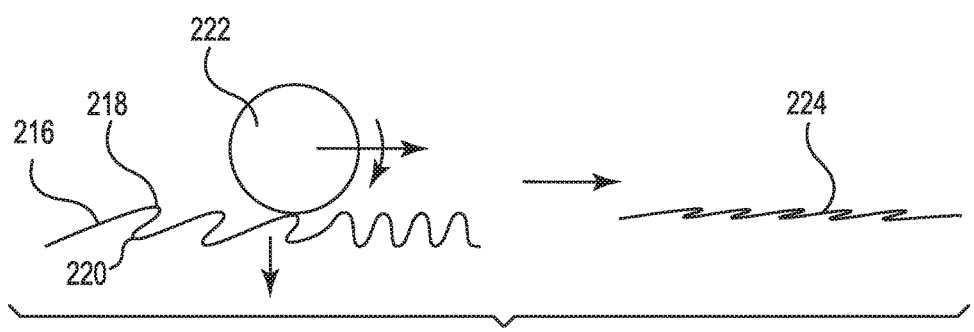
Fig. 2B

DENTAL APPLIANCES WITH SHAPED MATERIAL COMPONENTS

BACKGROUND

The present disclosure is related generally to the field of dental treatment. More particularly, the present disclosure is related to methods, instructions on a computing device readable medium, and devices formed with shaped material components.

Dental treatments may involve, for instance, restorative and/or orthodontic procedures. Restorative procedures may be designed to implant a dental prosthesis (e.g., a crown, bridge, inlay, onlay, veneer, etc.) intraorally in a patient.

Dental treatments also may include dental appliances in the form of trays that fit around the teeth of a jaw of a patient. These trays may hold medications to improve the health of the teeth or surrounding tissues or may be used to reduce a patient's sleep apnea of snoring.

Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems and other dental appliances can utilize materials that are light weight and/or transparent. With respect to aligners, these devices provide a set of appliances that can be used serially such that, as the teeth move, a new appliance can be implemented to further move the teeth without having to take a new impression of the patient's teeth at every increment of tooth movement in order to make the successive appliance.

In various instances, teeth of a patient's upper jaw and teeth of the patient's lower jaw may contact in an incorrect or suboptimal manner (e.g., crowding, crossbite, deep bite). A dental appliance can be provided to correct such an issue.

In some embodiments, these types of dental appliances may have the need to reinforce some areas or the whole appliance or that a specialized feature may be needed in a certain area of the dental appliance. For example, it may be desired that an area be reinforced to provide more force, force in one or more specific directions, or to provide force for an extended period of time. However, as these devices are typically formed from one sheet of material having a uniform thickness, reinforcement may not be possible.

BRIEF DESCRIPTION OF THE DRAWINGS

FIG. 1A illustrates an angled overhead view of a dental appliance of a patient being formed according to an embodiment of the present disclosure.

FIG. 1B illustrates an end view of a dental appliance for the lower jaw of a patient after formation according to the embodiment shown in FIG. 1A.

FIG. 2A illustrates an apparatus for forming a ribbed structure for providing reinforcement to a dental appliance surface utilizing a number of heating elements according to a number of embodiments of the present disclosure.

FIG. 2B illustrates an apparatus for flattening the ribbed structure to create a thickened area of a dental appliance according to a number of embodiments of the present disclosure.

DETAILED DESCRIPTION

Figure 2C:
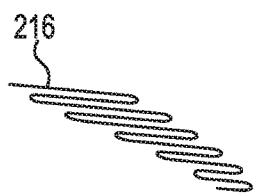
FIG. 2C illustrates an example of a flattened ribbed structure to create a thickened area of a dental appliance according to a number of embodiments of the present disclosure.

As discussed above, the present disclosure is related to methods, instructions on a computing device readable medium, and devices formed with folded material components. For example, one method of forming a dental appliance, includes forming a shell having a number of tooth apertures configured to receive and reposition a number of teeth of a patient along one jaw of a patient, the shell having a number of specialized components and wherein the number of specialized components are formed from folding multiple sections of the first sheet of material over each other to form the specialized component.

In this manner, specialized components such as thickened portions of a dental appliance, specially shaped portions like specialized cut areas, and/or spring type features can be created as will be discussed in more detail with respect to the figures provided herein.

The figures herein follow a numbering convention in which the first digit or digits correspond to the drawing figure number and the remaining digits identify an element or component in the drawing. Similar elements or components between different figures may be identified by the use of similar digits. For example, 314 may reference element "14" in FIG. 3, and a similar element may be referenced as 414 in FIG. 4.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

FIG. 1A illustrates an angled overhead view of a dental appliance for the lower jaw of a patient being formed according to an embodiment of the present disclosure. FIG. 1A shows an example of a type of reinforcement that can be accomplished using the techniques described herein. In the embodiment of FIG. 1A, the design includes a dental appliance 100 having a shell 102 with a tooth aperture 104 (although shown as an arch shape for simplicity of this application, the aperture can be tooth shaped to receive a number of teeth of a patient along one jaw of a patient). The shell has a specialized component in the form of a ribbed reinforcement 106 on the lingual side of the teeth of the jaw of the patient.

The specialized component can be used to form a reinforcement by folding multiple sections of the first sheet of material over each other as is shown in FIG. 1B. This formation can, for example, be accomplished by rolling a heated cylinder along the surface 111 of rib 106 to compress the rib thereby forming a reinforced structure.

As used herein, to be "folded over" may not mean above and below, but may also mean where the portions of the ribbed area (e.g., side walls 110 and 111 of rib 106 in the embodiment of FIGS. 1A and 1B) and at least a portion of the lingual side of the cavity receiving teeth (e.g., side 108 of cavity 104) would overlap each other as shown in FIG. 1B. In this manner, the ribbed section can be said to overlap the buccal side wall of the cavity for receiving teeth to reinforce the wall and/or add strength to other portions of the appliance or the appliance as a whole.

FIG. 1B illustrates an end view of a dental appliance for the lower jaw of a patient after formation according to the embodiment shown in FIG. 1A. This ribbed portion could be compressed in some embodiments such that the buccal (outer) surface of the cavity for receiving teeth and the outside surface of the inner s side of the rib can be touching or nearly touching as shown in FIG. 1B. Further, in some embodiments, the rib and the outer surface of the cavity can be connected together, such as by adhesive, mechanical attachment mechanisms, or other attachment processes to provide a reinforced surface.

FIG. 2A illustrates an apparatus for forming a ribbed structure for providing reinforcement to a dental appliance surface utilizing a number of heating elements according to a number of embodiments of the present disclosure. In the embodiment of FIG. 2A, a sheet of material 214-1 interacts with a set of heated elements 212 (in this case, six bar shaped elements each having a circular cross-section).

The set of elements can be comprised of one or more elements and their shape can be any suitable shape. For example, in FIG. 2A, the elements each have the same elongate length and circular cross-section, but in some embodiments, the cross-sectional shape may not be circular (e.g., solid triangle, a hollow triangle, a hollow circle, a semicircle, an arch, a rectangular shape, two angled surfaces that come together at a point, or any other suitable shape) and the elements may not be of the same shape (e.g., one or more of their elongate lengths may be different and/or their cross-sectional shapes may be different).

When the sheet interacts with the heated elements (in this example, when the heating elements are pressed onto the sheet or the sheet is pressed onto the elements, a resultant sheet 216 having a number of ribbed shapes (in some cases, the shape can be sinusoidal forming a number of peaks 218 and valleys 220) results. Such a shaping process can be utilized before forming the appliance or after forming the appliance (e.g., this technique may be employed on a portion of the appliance such as a side wall of the cavity for receiving teeth). Such structures may be used as a reinforcement structure or may be used as spring type structure, allowing flexibility in a linear, bending, or twisting direction based on the direction of orientation of the ribs to the forces placed thereon and/or the materials used.

In the embodiment shown in FIG. 2A, the sheet of material 214-1 is bowed to allow for the ribs to be formed, but in some embodiments, the sheet can be planar and the material either thinned or the overall length of the sheet shortened to create the ribs. Even in embodiments where the material is thinned, the resultant structure may be thicker than a non-ribbed structure and/or be more reinforced than a non-ribbed structure, particularly in a direction perpendicular to the direction of elongation of the ribs.

FIG. 2B illustrates an apparatus for flattening the ribbed structure to create a thickened area of a dental appliance according to a number of embodiments of the present disclosure. As shown in FIG. 2B, the resultant ribbed structure (e.g., such as that formed by the process of FIG. 2A) can be flattened to create a reinforced area.

This reinforced area is effectively made thicker by laying the ribs onto each other. Such a technique creates a surface that may comprise two or more layers of material onto each other.

Although not limited to this technique, as can be seen from the example of FIG. 2B, the laying over of the ribs can be accomplished by positioning a flattening member 222 in contact with a surface of the ribbed sheet 216 causing the peaks 218 of the ribs to lay onto one or more other peaks and/or onto one or more of the valleys 220. In this manner, multiple layers of material will be adjacent one another, thereby creating a thickened overall structure 224 that can provide reinforcement, for example.

FIG. 2C illustrates an example of a flattened ribbed structure to create a thickened area of a dental appliance according to a number of embodiments of the present disclosure. As shown in FIG. 2C a sheet of material 216 has been folded multiple times such that the structure when compressed will include multiple portions of the sheet along some portions (for example, as many as seven portions of the sheet are compressed together in some portions of the embodiment of FIG. 2C).

Figure 2D:
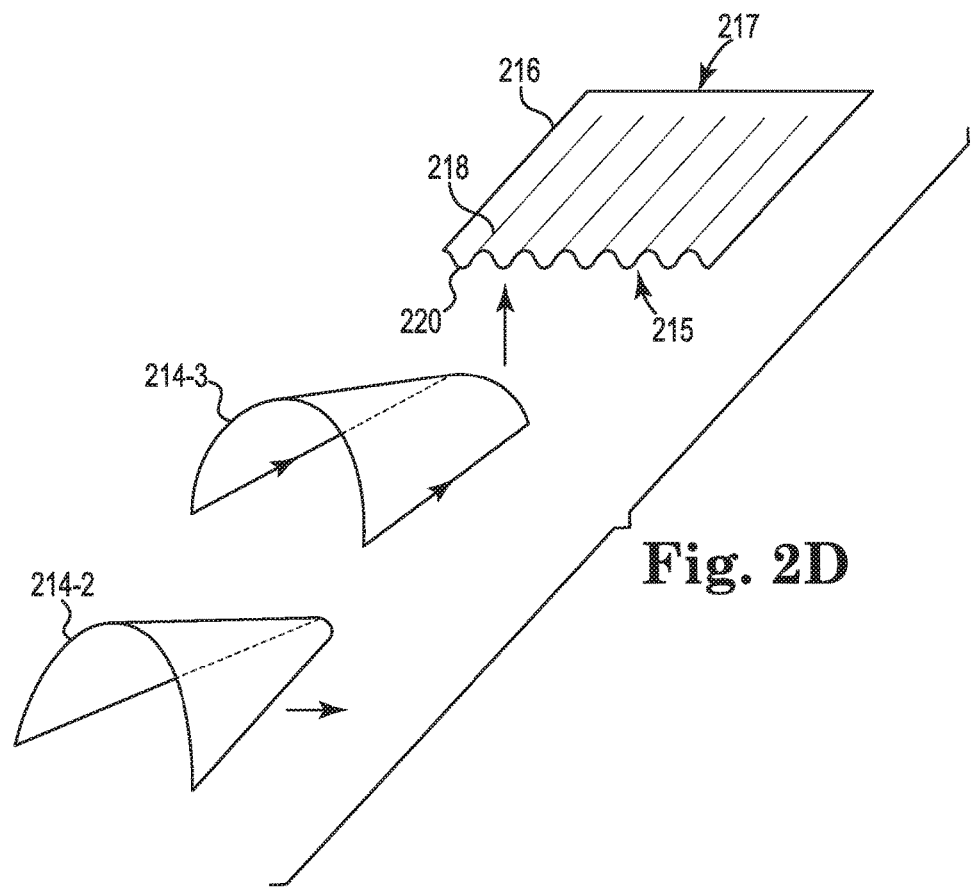
FIG. 2D illustrates an example of a ribbed structure formed from a cone or truncated cone to create ribbed area on one portion of a sheet of material that can be used to form a dental appliance according to a number of embodiments of the present disclosure.

FIG. 2D illustrates an example of a ribbed structure formed from a cone or truncated cone to create ribbed area on one portion of a sheet of material that can be used to form a dental appliance according to a number of embodiments of the present disclosure. In some embodiments, a sheet in the form of a cone or truncated cone can be formed, for example, with elements 212 to create a structure that has a non-uniform pattern across its surface. For example, in FIG. 2D, a cone shaped sheet of material 214-2 and a truncated cone of material 214-3 are shown.

An example of a resultant formed sheet is shown in the top image of FIG. 2D. In that image, the sheet 216 has a number of peaks 218 and valleys 220 that gradually diminish from a first edge of the sheet 215 to a second edge of the sheet 217. Although the peaks and valleys are shown being generally parallel, it will be understood that the larger the radius of the base of the cone shape or truncated cone shape is as compared to the top of the cone or truncated cone, the more angled the peaks and valleys will be with respect to each other.

Figure 3:
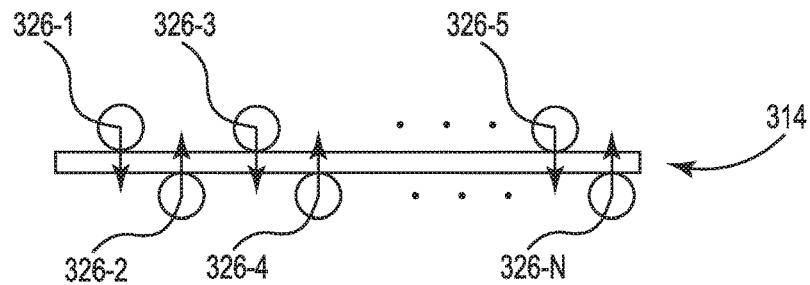
FIG. 3 illustrates another apparatus for forming a ribbed structure for providing reinforcement to a dental appliance surface utilizing a number of heating elements according to a number of embodiments of the present disclosure.

FIG. 3 illustrates another apparatus for forming a ribbed structure for providing reinforcement to a dental appliance surface utilizing a number of heating elements according to a number of embodiments of the present disclosure. In the embodiment of FIG. 3, a number of shaping elements 326-1, 326-2, 326-3, 326-4, 326-5, and 326-N are positioned on either side of the surface of the sheet of material to be structured (e.g., in the example shown in FIG. 3 above and below the surface). In some embodiments, the shaping elements on one side of the sheet can be moved toward the sheet, thereby deforming the sheet as they interact with the surface of the sheet.

This movement can cause the sheet to interact with the shaping elements on the other side of the sheet which may cause further deformation. Further, in some embodiments, the shaping elements can be moved toward the sheet of material 314, thereby creating an undulating surface. As discussed above, the shaping elements can be heated to encourage the formation of the sheet of material. A flattening member, such as that shown in FIG. 2B can be used on the shapes formed using the embodiments of FIG. 3 creating a thickened overall structure, such as that shown at 224 of FIG. 2B.

Figure 4:
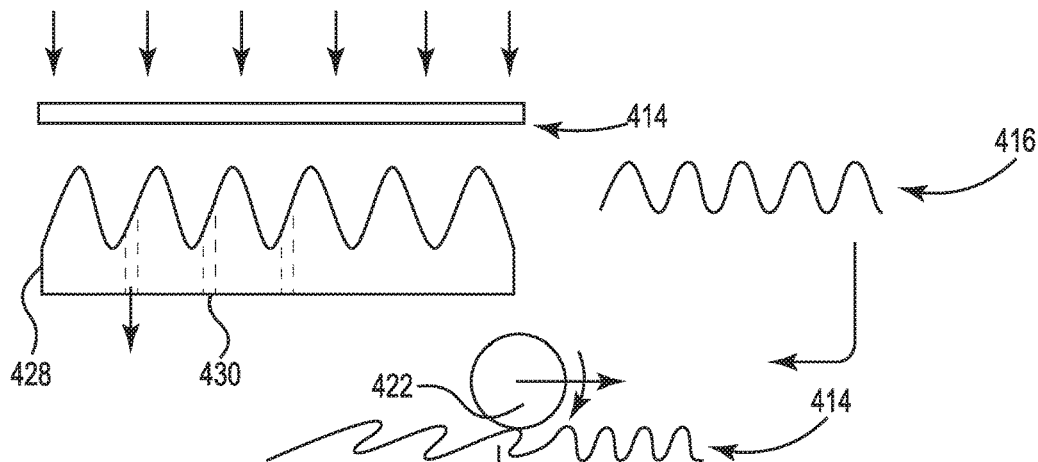
FIG. 4 illustrates another apparatus for forming a ribbed structure for providing reinforcement to a dental appliance surface utilizing a number of heating elements according to a number of embodiments of the present disclosure.

FIG. 4 illustrates another apparatus for forming a ribbed structure for providing reinforcement to a dental appliance surface utilizing a number of heating elements according to a number of embodiments of the present disclosure. In the embodiment of FIG. 4, a sheet of material 414 is applied over a shape template 428 that has a desired shape for the formation of the sheet. In this example, the shape of the formed sheet is shown at 416.

In order to get the sheet to engage the surface of the template 428, the sheet can be force downward by a structure that has a mating shape to that of the template 428 (a shape similar to 428, but with the peaks facing toward the valleys of the template 428). In some embodiments, the template can include a number of apertures 430 that can allow the use of a vacuum force on the sheet to suck the sheet onto the surface of the template as is shown in FIG. 4.

As discussed in the above embodiments, a flattening member 422 can be used to create a thickened overall structure, as shown at 414 of FIG. 4. As shown in FIG. 4, in some embodiments, the flattening member can rotate as it flattens the sheet 414. The flattening member can also move along the surface of the sheet or the sheet can move along the surface of the flattening member to flatten the surface of the sheet.

Figure 5:
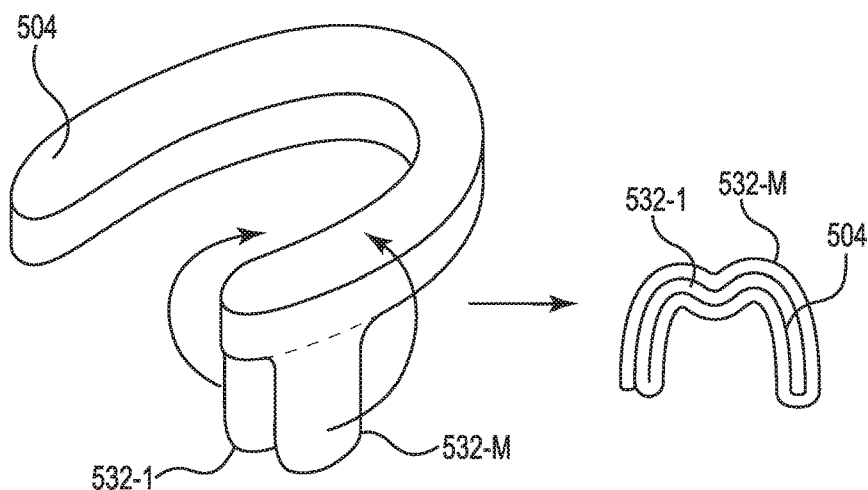
FIG. 5 illustrates a dental appliance having flaps that can be folded to create a thicker portion of the dental appliance according to a number of embodiments of the present disclosure.

FIG. 5 illustrates a dental appliance having flaps that can be folded to create a thicker portion of the dental appliance according to a number of embodiments of the present disclosure. In the embodiment of FIG. 5, the shell of the dental appliance has a first thickness of material 504 that forms the one or more cavities shaped to accommodate one or more teeth of a patient.

In the example of FIG. 5, there is one cavity that accommodates all of the teeth on one jaw of a patient. The embodiment of FIG. 5 also includes a reinforced portion wherein the reinforcement is provided by excess material sections 532-1 and 532-M that are bent onto a surface of the first thickness of material 504. As shown in the right image of FIG. 5, once bent onto the first thickness 504 (which is a cavity shape to accommodate a tooth), the excess material sections 532-1 and that 532-M reinforce that section of the shell of the dental appliance. In various embodiments, more than one section of the shell can be reinforced in this manner. Further, in some embodiments, the reinforcement can be accomplished through use of one excess material section.

Figure 6:
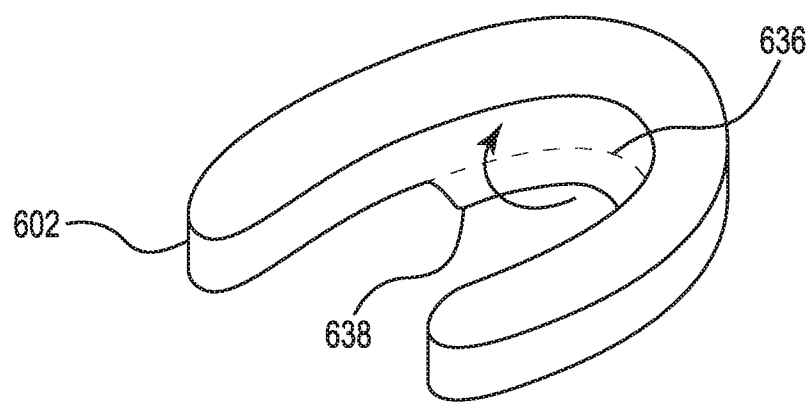
FIG. 6 illustrates another dental appliance having a flap that can be folded to create a thicker portion of the dental appliance according to a number of embodiments of the present disclosure.

FIG. 6 illustrates another dental appliance having a flap that can be folded to create a thicker portion of the dental appliance according to a number of embodiments of the present disclosure. In the embodiment of FIG. 6, the shell 602 includes an excess material section 638. The excess material section and the main part of the shell body are attached at transition 636. This can allow for the excess material section 638 to be bent at transition 636 toward the shell 602 to reinforce a portion thereof.

In some embodiments, the transition 636 can include one or more physical characteristics to assist in allowing the excess material section to be bent with respect to the shell. For example, the material at the transition can be thinned, scored, or have any other suitable characteristic to better allow it to be bent such that it can reinforce a portion of the shell 602.

Figure 7:
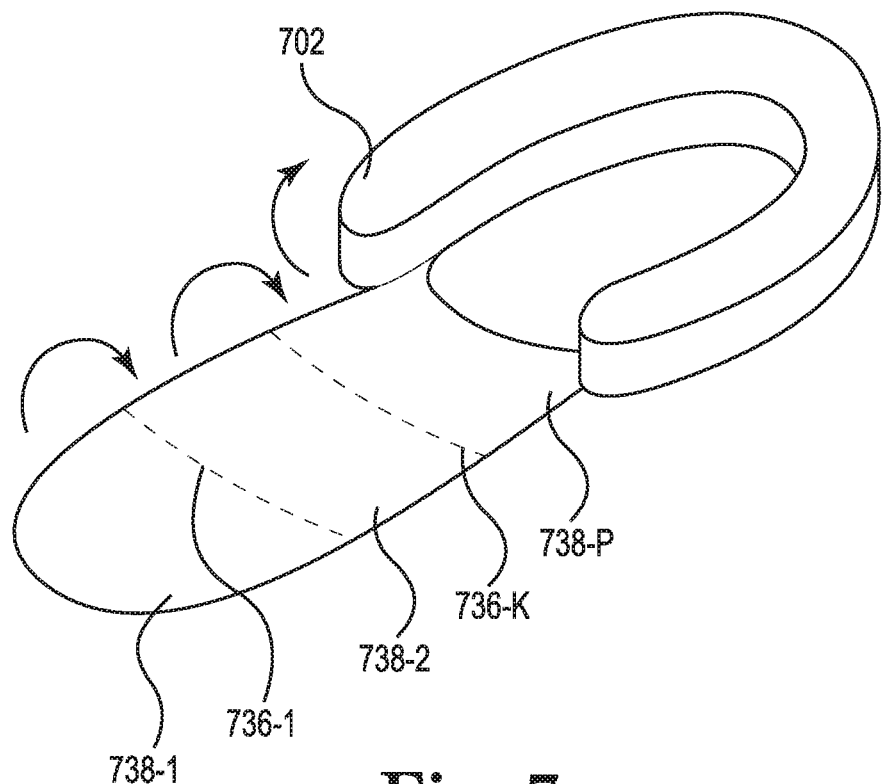
FIG. 7 illustrates another dental appliance having a flap that can be folded to create a thicker portion of the dental appliance according to a number of embodiments of the present disclosure.

FIG. 7 illustrates another dental appliance having a flap that can be folded to create a thicker portion of the dental appliance according to a number of embodiments of the present disclosure. In FIG. 7, the shell 702 includes excess material sections 738-1, 738-2, and 738-P. These portions are separated by transitions 736-1, 736-2, and 736-K.

In this embodiment, the excess material portions are not used to thicken a portion of the shell having the cavities for accommodating teeth, but rather, are used to form an addition feature of the shell 702. In the example of FIG. 7, the excess material sections 738-1, 738-2, and 738-P are folded to create an arch or palate expansion structure that can be used to expand the arch of the patient (through movement of the teeth) or expansion of the palate (through movement of the palate).

Figure 8A:
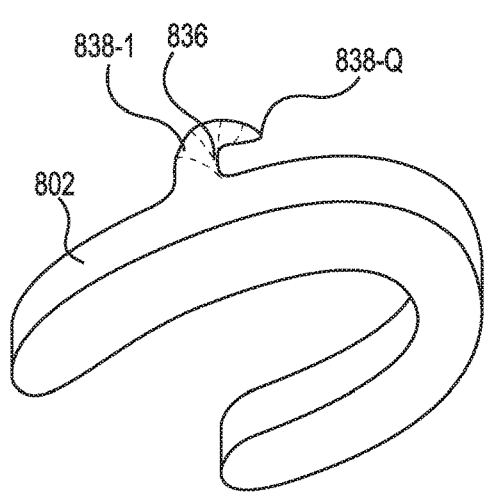
FIG. 8A illustrates another dental appliance having a flap that can be folded to create a thicker portion of the dental appliance for use as a precision cut feature of the dental appliance according to a number of embodiments of the present disclosure.

FIG. 8A illustrates another dental appliance having a flap that can be folded to create a thicker portion of the dental appliance for use as a precision cut feature of the dental appliance according to a number of embodiments of the present disclosure. In the embodiment of FIG. 8A, the excess material sections 838-1 and 838-Q are used to form an additional type of feature to be used on the shell 802.

In this example, a hook 836 is formed by having multiple specially shaped excess material sections folded over each other to form the hook shape shown. The dashed lines represent the shapes of the sections that were folded over to create the hook feature. Such a technique could be used to provide many features that are traditionally accomplished through use of precision post formation cutting. Such an approach can save time and reduce manufacturing steps, in some implementations.

Figure 8C:
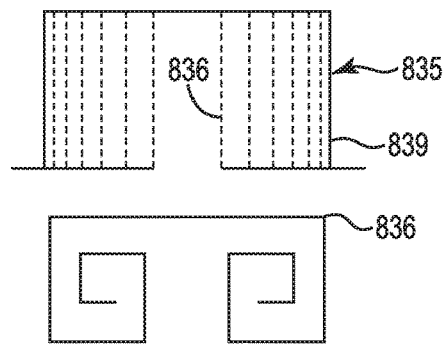
FIG. 8C illustrates a structure that can be used in a dental appliance having a squared roll portion according to a number of embodiments of the present disclosure.
Figure 8B:
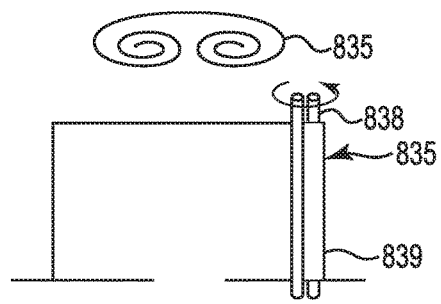
FIG. 8B illustrates a structure that can be used in a dental appliance having a curled portion according to a number of embodiments of the present disclosure.

FIG. 8B illustrates a structure that can be used in a dental appliance having a curled portion according to a number of embodiments of the present disclosure. As shown in the bottom part of FIG. 8B, a sheet of material (such as that used to form the dental appliance 835) can be rolled over itself several times to form a curled design. As shown in the example of FIG. 8B, a number of rolled formations can be made using this technique.

In the embodiment shown, the rolling is accomplished by positioning the sheet of material 835 between two rollers 838 and the rollers are turned to roll the material around the rollers. As discussed above, this can be utilized to accomplish a single roll of material (e.g., such as the left or right side of the top drawing of FIG. 8B) or can be used to form multiple rolled structures as shown in the top image of FIG. 8B.

FIG. 8C illustrates a structure that can be used in a dental appliance having a squared roll portion according to a number of embodiments of the present disclosure. As shown in the bottom part of FIG. 8C, a sheet of material (such as that used to form the dental appliance 835) can be rolled over itself several times to form a square rolled design.

In such embodiments, the squared design is bent at each of the dashed lines 836 to form portions that are angled with respect to each other as shown in FIG. 8C. For example, the bottom image of FIG. 8C shows bends 836 that form 90 degree angles between two adjacent portions of the sheet.

To accomplish such a design, the scored portions 836 (shown in the top image of FIG. 8C), are staggered at different distances between each other such that a squared roll can be formed (shown in the bottom image of FIG. 8C, not to scale). As shown in the example of FIG. 8C, a number of rolled formations (in the example shown, two formations are created) can be made using this technique.

Such shapes can be accomplished, for example, by creating the sheet of material with one or more score lines to aid in the rolling of the sheet. For example, as shown in the example of FIG. 8C, the score lines can be thinner portions 836 or can be perforations through the sheet 835.

In various embodiments, folds can be created that are at an angle to a surface (e.g., 45 degrees to a surface). Also, in some embodiments, a sheet of material can be folded in a first direction and then that folded material can be folded in a second direction (e.g., folding a sheet parallel to an edge of the sheet and then folding that folded portion at an angle 35 degrees to the edge of the sheet). For example, in FIG. 8C, instead of bending the sheet to form a squared roll, the portions of the sheet can be folded over onto each other at lines 836 which are parallel to edge 839 to form a layered structure and then that resultant layered structure can be folded at an angle (e.g., 55 degrees) with respect to the edge 839.

Figure 9:
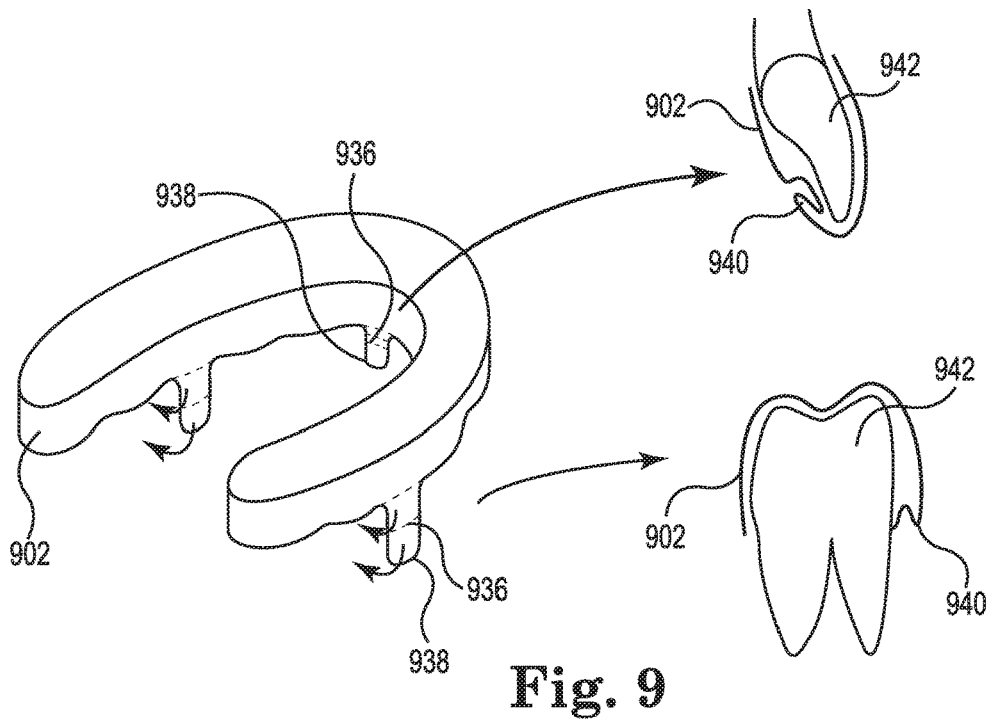
FIG. 9 illustrates another dental appliance having a flap that can be folded to create a thicker portion of the dental appliance for use as spring features of the dental appliance according to a number of embodiments of the present disclosure.

FIG. 9 illustrates another dental appliance having a flap that can be folded to create a thicker portion of the dental appliance for use as spring features of the dental appliance according to a number of embodiments of the present disclosure. In the embodiment of FIG. 9, the shell 902 includes a number of excess material sections 938 that can be bent at a number of transitions 936 to form one or more springs (in the example of FIG. 9, three springs are formed). As shown in the images to the right, in such embodiments, the spring can be formed from folding the excess material sections as shown in the lower left image wherein an edge of one section contacts the surface of a tooth to provide the spring force.

In the upper left image embodiment, the spring is formed by material being bent toward the tooth, but continuing to an end that is not part of the spring, but rather forms a side of a cavity for placing a tooth therein. The springs can provide several functions. For example, the springs can function to provide specialized force for movement of teeth with a larger working range (i.e., distance that the tooth can be moved), they can also provide cushioning to make the appliance more comfortable. Springs can also be used in other ways, as shown in FIG. 10.

Figure 10:
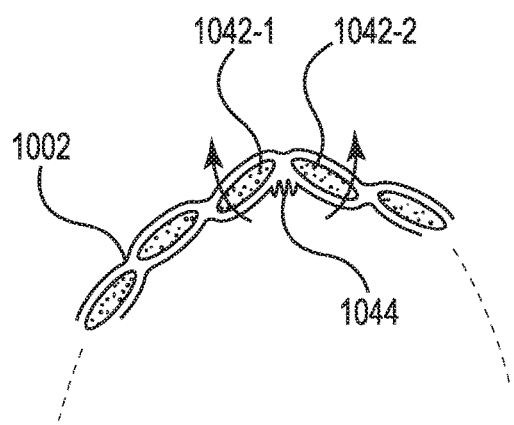
FIG. 10 illustrates another dental appliance having a spring feature of a dental appliance according to a number of embodiments of the present disclosure.

FIG. 10 illustrates another dental appliance having a spring feature of a dental appliance according to a number of embodiments of the present disclosure. In the embodiment of FIG. 10, the spring 1044 is formed between two tooth apertures for receiving teeth 1042-1 and 1042-2. The apertures are part of the cavity for receiving teeth formed in the shell 1002. In such an embodiment, the spring 1044 can be used to provide a cushioning force as the teeth are straightened or can provide a specialized force to assist in moving the teeth 1042-1 and 1042-2.

Figure 11:
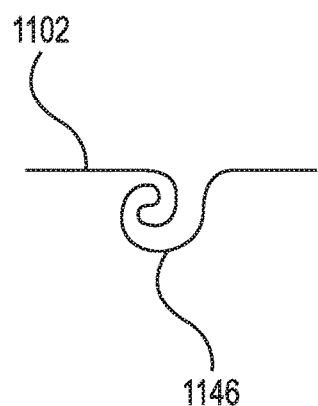
FIG. 11 illustrates a dental appliance having a hinge feature of a dental appliance according to a number of embodiments of the present disclosure.

FIG. 11 illustrates a dental appliance having a hinge feature of a dental appliance according to a number of embodiments of the present disclosure. The techniques described herein can be utilized to create other specialized features. For example, a curl 1146 can be formed in the shell 1102 through use of a form created in a curled shaped wherein the sheet can be forced into the shape by folding the sheet through application of heat and a bending force to bend the sheet to create a fold or part of the sheet can be pulled into the form via a vacuum.

Figure 12:
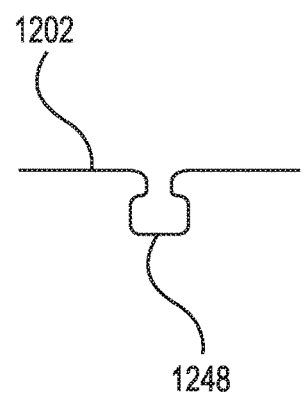
FIG. 12 illustrates another dental appliance having a hinge feature of a dental appliance according to a number of embodiments of the present disclosure.

FIG. 12 illustrates another dental appliance having a hinge feature of a dental appliance according to a number of embodiments of the present disclosure. As discussed with respect to the curled formation, the techniques described herein can be utilized to create other specialized features, such as that shown in FIG. 12. In this embodiment a T-shape 1248 can be formed in the shell 1202 through use of a form created in a T-shape wherein the sheet can be forced into the shape or can be pulled into the form via a vacuum.

Figure 13A:
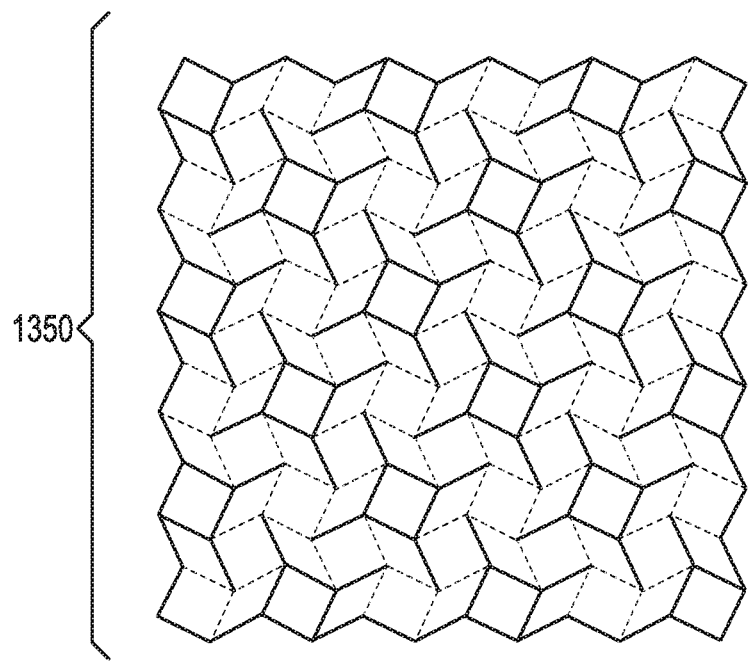
FIG. 13A illustrates a technique of forming a sheet to allow the sheet to be folded into specific three dimension shapes.
Figure 13A:
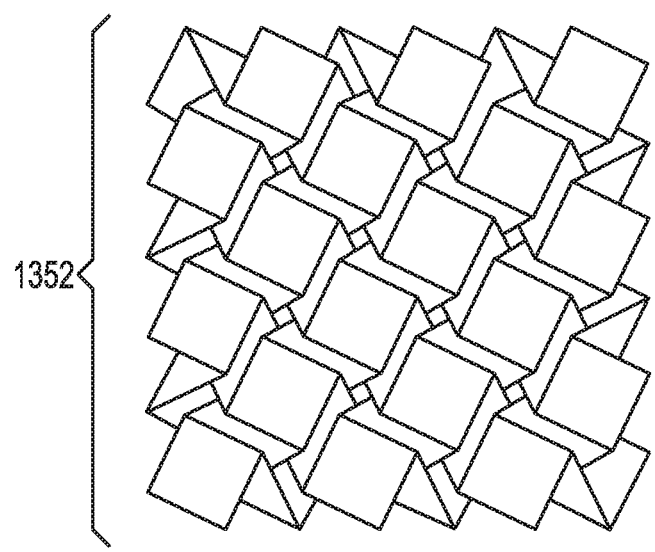

FIG. 13A illustrates a technique of forming a sheet to allow the sheet to be folded into specific three dimension shapes. In the examples shown in FIG. 13A, the top pattern 1350 can be formed on the sheet of material and the pattern can then be expanded into a three dimensional shape as shown at 1352 of FIG. 13A.

As can be seen from the example of FIG. 13A, the shapes made can be in many patterns and the resultant three dimensional shapes can be very diverse. In some embodiments, the pattern can be formed by scoring, thinning, or cutting through the material along the lines shown in any of the patterns at 1350. The shapes can then be bent along the lines inward or outward with respect to the adjacent pieces to form desired three dimensional shapes.

Figure 13B:
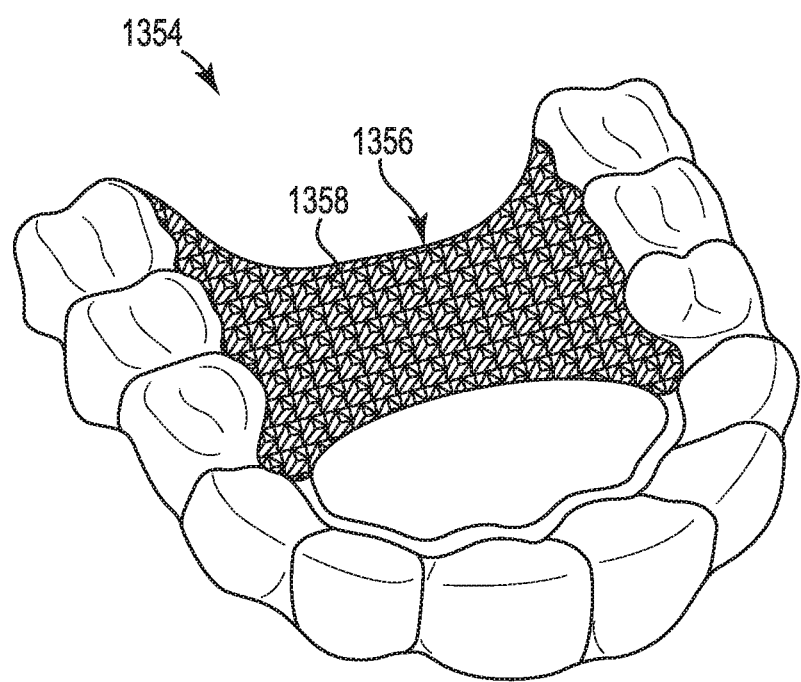
FIG. 13B illustrates a dental appliance having a patterned surface similar to those shown in FIG. 13A and formed according to a number of embodiments of the present disclosure.

FIG. 13B illustrates a dental appliance having a patterned surface similar to those shown in FIG. 13A and formed according to a number of embodiments of the present disclosure. As shown in this Figure, the shaped portion can be formed as described above to change the properties and/or the geometry (e.g., provide added rigidity) to the portion of the appliance on which it is applied (for example, the patterned surface 1358 can be formed on the palatal arch portion 1356 of the appliance 1354 of FIG. 13B among other applications).

Figure 14:
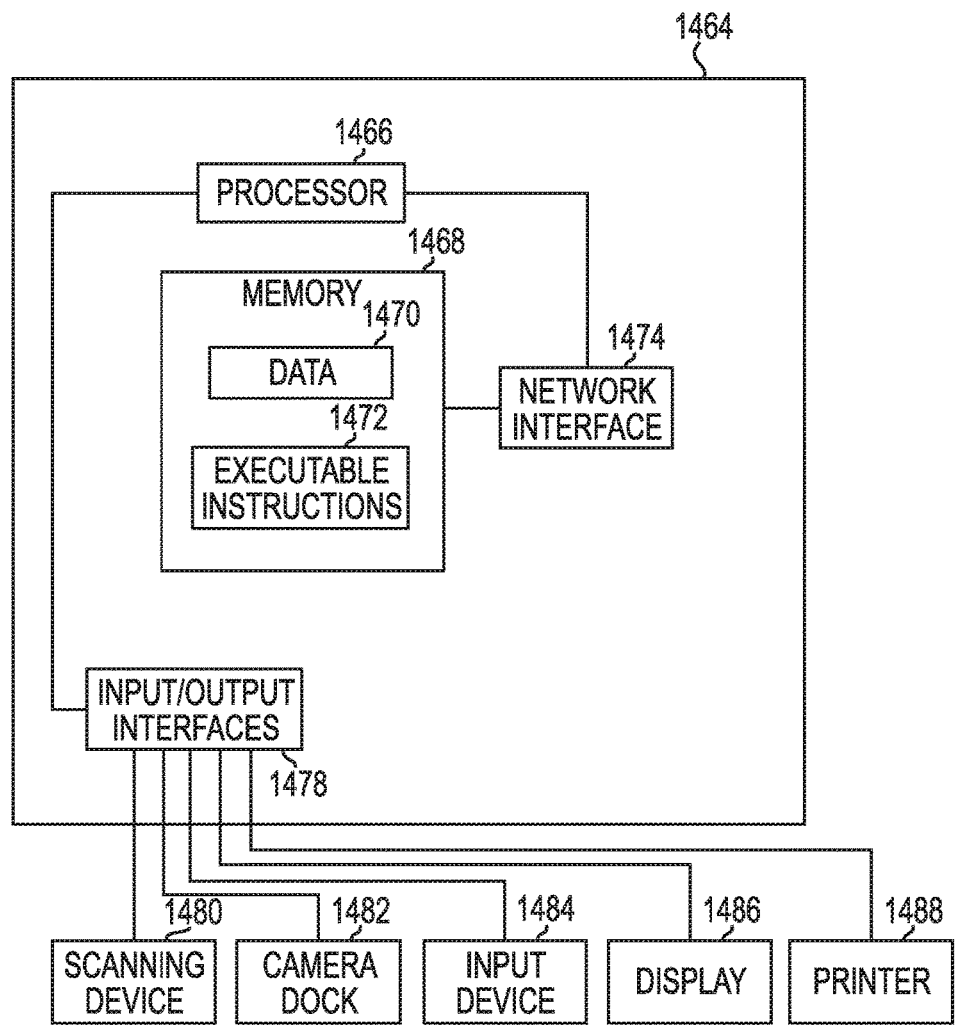
FIG. 14 illustrates an example computing device readable medium having executable instructions that can be executed by a processor to perform a method according to one or more embodiments of the present disclosure.

FIG. 14 illustrates an example computing device readable medium having executable instructions that can be executed by a processor to perform a method according to one or more embodiments of the present disclosure. For instance, a computing device 1464 can have a number of components coupled thereto. The computing device 1464 can include a processor 1466 and a memory 1468. The memory 1468 can have various types of information including data 1470 and executable instructions 1472, as discussed herein.

The processor 1466 can execute instructions 1472 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 1468 and/or the processor 1466 may be located on the computing device 1464 or off the computing device 1464, in some embodiments. As such, as illustrated in the embodiment of FIG. 14, the computing device 1464 can include a network interface 1474. Such an interface 1474 can allow for processing on another networked computing device, can be used to obtain information about the patient, and/or can be used to obtain data and/or executable instructions for use with various embodiments provided herein.

As illustrated in the embodiment of FIG. 14, the computing device 1464 can include one or more input and/or output interfaces 1478. Such interfaces 1478 can be used to connect the computing device 1464 with one or more input and/or output devices 1480, 1482, 1484, 1486, 1488.

For example, in the embodiment illustrated in FIG. 14, the input and/or output devices can include a scanning device 1480, a camera dock 1482, an input device 1484 (e.g., a mouse, a keyboard, etc.), a display device 1486 (e.g., a monitor), a printer 1488, and/or one or more other input devices. The input/output interfaces 1478 can receive executable instructions and/or data, storable in the data storage device (e.g., memory), representing a virtual dental model of a patient's dentition.

In some embodiments, the scanning device 1480 can be configured to scan one or more physical dental molds of a patient's dentition. In one or more embodiments, the scanning device 1480 can be configured to scan the patient's dentition and/or dental appliance directly. The scanning device 1480 can be configured to input data into the computing device 1464.

In some embodiments, the camera dock 1482 can receive an input from an imaging device (e.g., a 2D or 3D imaging device) such as a digital camera, a printed photograph scanner, and/or other suitable imaging device. The input from the imaging device can, for example, be stored in memory 1468.

The processor 1466 can execute instructions to provide a visual indication of a treatment plan, a dental appliance, and/or a repositioning jaw element on the display 1486. The computing device 1464 can be configured to allow a treatment professional or other user to input treatment goals. Input received can be sent to the processor 1466 as data 1470 and/or can be stored in memory 1468.

Such connectivity can allow for the input and/or output of data and/or instructions among other types of information. Some embodiments may be distributed among various computing devices within one or more networks, and such systems as illustrated in FIG. 14 can be beneficial in allowing for the capture, calculation, and/or analysis of information discussed herein.

The processor 1466, in association with the data storage device (e.g., memory 1468), can be associated with the data 1470. The processor 1466, in association with the memory 1468, can store and/or utilize data 1470 and/or execute instructions 1472 for determining a shape of a shell of a virtual model of a dental appliance. Such data can include the virtual dental model. The virtual model of the dental appliance with the specialized shape can be used to create a physical dental appliance, for instance, as discussed further herein.

The processor 1466 coupled to the memory 1468 can cause the computing device 1464 to perform a method including, for example, designing a virtual template for the formation of a shell having a number of tooth apertures configured to receive and reposition a number of teeth of a patient along one jaw of a patient, the shell having a number of specialized components and wherein the number of specialized components are formed from folding multiple sections of the first sheet of material over each other. The multiple sections of the first sheet of material can be created in a virtual manner so that the designer of the appliance can determine the proper shape for those sections to be used to create the specialized components.

In some embodiments, the method of forming a dental appliance can include forming the shell having a first sheet of material for use in forming a particular specialized component and bending a portion of the first sheet of material over itself to form first and second folded layers of material. Such a method can be virtually tested to ensure that the bending of the portion of the first sheet will create the desired shape.

Forming the shell having a first sheet of material for use in forming a particular specialized component can, for example, include forming the first sheet with a score line thereon. The score line can, for example, be used for facilitating the folding of the sheet at the score line.

This can be accomplished while the sheet of material is still in a formable state. As used herein, the formable state of the material can be accomplished via use of an external stimulus to change the state of the material such as through use of chemical, temperature, microwave, and/or pressure. The formation of the score lines can be determined in a virtual model which may be beneficial, for example, in determining whether scoring of the dental appliance will allow for the proper folding characteristics.

The formation of the appliance can also include folding the sheet at the score line by applying heat to the score line to transition the material at the score line to a formable state.

A dental appliance can be made, for example, by thermal-forming a sheet of plastic over a physical dental mold. The physical dental mold, for instance, can represent an incremental position to which a patient's teeth are to be moved. The physical dental mold can be manufactured by downloading a computer-aided Design (CAD) virtual dental model to a rapid prototyping process, such as, for example, a computer-aided manufacturing (CAM) milling, stereolithography, and/or photolithography. The virtual dental mold can be hollowed out before being sent for manufacturing to save on material cost, for example.

The dental mold (e.g., set of molded teeth) can be created from a virtual model of a number of teeth of a patient. A virtual model, for example, can include an initial virtual dental model and/or intermediate virtual dental model. A dental mold can be formed in accordance with a unique treatment file that identifies a patient, a stage of a treatment plan, the virtual model of the number of teeth, and/or whether the dental mold is of the upper and/or lower dental arch.

In some embodiments, a treatment file can be accessed by a rapid prototyping apparatus machine, such as a SLA or 3D printing, to form and/or create the dental mold. The result of the dental mold can include a set of molded teeth. The set of molded teeth can include at least a replica of the number of teeth of the patient. The dental mold can be used to make a dental appliance, for example, by creating a negative impression of the dental mold using polymeric sheets of material and vacuum forming the sheets over the dental mold, as discussed above.

For instance, a dental appliance can be formed by layering a thermoformable sheet of material and/or multiple sheets of one or more materials over the dental mold. The materials can include a polymeric material, for instance. Generally, the dental appliance is produced and/or formed by heating the polymeric thermoformable sheet and vacuum or pressure forming the sheet over the dental mold (e.g., a number of molded teeth). The shape of the sheet of material can change thickness on some portions of the sheet as it conforms to the mold shape. A dental appliance can, for example, include a negative impression of the dental mold. The appliance and/or parts thereof may be transparent, semi-transparent, or opaque in such a way as to emulate a nature tooth shade.

However, embodiments in accordance with present disclosure are not so limited. For example, embodiments in accordance with the present disclosure can include forming a dental appliance utilizing a variety of techniques, such as SLA or 3D printing, among other techniques.

In a number of embodiments, the processor 1466 coupled to the memory 1468 can cause the computing device 1464 to perform the method of providing a treatment plan. One or more appliances, including positioners, retainers, removable dental appliances, and/or other appliances for finishing and maintaining teeth positioning, can be utilized by a treatment professional in performing a treatment plan. The treatment plan can include the use of one or more dental appliances, as described herein.

As discussed above, a computing device can be used to create a virtual model and/or machine executable instructions for creating a physical model or direct fabrication (three dimensional printing or other direct manufacturing process) for the creation of the shells described herein. For example, in one embodiment, a removable dental appliance formation system includes a non-transitory computing device readable medium storing instructions executable by a processor to cause a computing device to perform a method.

In some embodiments, the non-transitory computing device readable medium storing instructions include instructions for fabricating a physical model for forming at least the first shell. The system can also include a dental mold formation apparatus (thermo-forming device, three dimensional printing device, etc.) for receiving the instructions for fabricating the physical model and applying one or more materials to fabricate the physical model.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of forming a dental appliance with a shaped specialized component, comprising:
   forming a shell having a number of tooth apertures configured to receive and reposition a number of teeth of a patient along one jaw of a patient, the shell having a number of specialized components and wherein the number of specialized components are formed from folding multiple sections of a first sheet of material over each other.

2. The method of forming a dental appliance of claim 1, wherein the method includes:
   forming the shell having a first sheet of material for use in forming a particular specialized component; and
   bending a portion of the first sheet of material over itself to form first and second folded layers of material.

3. The method of forming a dental appliance of claim 2, wherein forming the shell having a first sheet of material for use in forming a particular specialized component includes forming the first sheet with a score line thereon for facilitating the folding of the sheet at the score line.

4. The method of forming a dental appliance of claim 3, wherein the method further includes folding the sheet at the score line while the sheet of material is still in a formable state.

5. The method of forming a dental appliance of claim 3, wherein the method further includes folding the sheet at the score line by applying heat to the score line to transition the material at the score line to a formable state.

6. The method of forming a dental appliance of claim 3, wherein bending a portion of the first sheet of material over itself to form first and second folded layers of material includes forming a number of waveform shapes in the sheet of material wherein the sinusoidal shapes have number of peaks and valleys in the sheet of material and then applying a force to lay at least one peak over onto at least one other peak to create a variable thickness of material.

7. The method of forming a dental appliance of claim 6, wherein applying a force to lay at least one peak over onto at least one other peak includes applying a force with a roller mechanism.

8. The method of forming a dental appliance of claim 2, wherein bending a portion of the first sheet of material over itself to form first and second folded layers of material includes forming a number of sinusoidal shapes in the sheet of material wherein the sinusoidal shapes have number of peaks and valleys in the sheet of material and then applying a force to lay at least one peak over onto at least one valley.

9. The method of forming a dental appliance of claim 8, wherein applying a force to lay at least one peak over onto at least one valley includes applying a force with a roller mechanism.

10. The method of forming a dental appliance of claim 2, wherein bending a portion of the first sheet of material over itself to form first and second folded layers of material includes imparting a force while bending the portion of the first sheet of material to create a spring from the first and second folded layers of material.

11. A method of forming a dental appliance, comprising:
forming a shell having a number of tooth apertures configured to receive and reposition a number of teeth of a patient along one jaw of a patient and having a first sheet of material extending outward from the shell; and
folding multiple sections of the first sheet of material over each other to form one or more specialized features having a thickness that is thicker than the thickness of the material forming the tooth apertures.

12. The method of forming a dental appliance of claim 11, wherein the method includes:
forming the shell having a first sheet of material for use in forming a particular specialized component; and
bending a portion of the first sheet of material over itself to form first and second folded layers of material.

13. The method of forming a dental appliance of claim 12, wherein bending a portion of the first sheet of material over itself to form first and second folded layers of material includes forming a number of peaks and valleys in the sheet of material and then applying a force to lay at least one peak over onto at least one valley.

14. The method of forming a dental appliance of claim 12, wherein bending a portion of the first sheet of material over itself to form first and second folded layers of material includes forming a number of peaks and valleys in the sheet of material and then applying a force to lay at least one peak over onto at least one other peak.

15. The method of forming a dental appliance of claim 12, wherein bending a portion of the first sheet of material over itself to form first and second folded layers of material includes forming a number of peaks and valleys in the sheet of material by positioning multiple elongate elements against at least one surface of the first sheet of material.

16. The method of forming a dental appliance of claim 12, wherein bending a portion of the first sheet of material over itself to form first and second folded layers of material includes forming a number of peaks and valleys in the sheet of material by positioning at least one surface of the first sheet of material against a surface of a template in which the surface has a peak and valley shape.

* * * * *